(12) United States Patent
Kraemer et al.

(10) Patent No.: US 10,460,848 B2
(45) Date of Patent: Oct. 29, 2019

(54) DEVICE FOR SUSPENDING AN X-RAY GRID, ARRANGEMENT WITH AN X-RAY GRID AND METHOD FOR OPERATING AN X-RAY GRID

(71) Applicant: SIEMENS HEALTHCARE GMBH, Erlangen (DE)

(72) Inventors: Alexander Kraemer, Irchenrieth (DE); Thomas Weber, Hausen (DE); Josef Zeidler, Marktredwitz (DE)

(73) Assignee: Siemens Healthcare GmbH, Erlangen (DE)

( * ) Notice: Subject to any disclaimer, the term of this patent is extended or adjusted under 35 U.S.C. 154(b) by 310 days.

(21) Appl. No.: 15/622,345

(22) Filed: Jun. 14, 2017

(65) Prior Publication Data

US 2017/0358379 A1     Dec. 14, 2017

(30) Foreign Application Priority Data

Jun. 14, 2016   (DE) .......................... 10 2016 210 529

(51) Int. Cl.
| | | |
|---|---|---|
| *G21K 5/08* | (2006.01) | |
| *G21K 1/02* | (2006.01) | |
| *A61B 6/00* | (2006.01) | |
| *G21K 1/06* | (2006.01) | |

(52) U.S. Cl.
CPC ............ *G21K 1/025* (2013.01); *A61B 6/4291* (2013.01); *A61B 6/4429* (2013.01); *A61B 6/484* (2013.01); *A61B 6/58* (2013.01); *G21K 1/06* (2013.01); *A61B 6/4441* (2013.01); *G21K 2207/005* (2013.01)

(58) Field of Classification Search
CPC ........ A61B 6/4291; A61B 6/06; A61B 6/5282
See application file for complete search history.

(56) References Cited

U.S. PATENT DOCUMENTS

| | | | |
|---|---|---|---|
| 7,857,511 B2 | 12/2010 | Hesl et al. | |
| 2010/0014225 A1* | 1/2010 | Reina | G21K 1/025 |
| | | | 361/679.01 |
| 2015/0243398 A1* | 8/2015 | Nam | A61B 6/4291 |
| | | | 378/62 |

FOREIGN PATENT DOCUMENTS

DE        102004061506 A1     6/2006

* cited by examiner

*Primary Examiner* — Don K Wong

(74) *Attorney, Agent, or Firm* — Laurence Greenberg; Werner Stemer; Ralph Locher

(57) ABSTRACT

A device for suspending an x-ray grid has a first rotating frame which can be rotated about a first axis. The x-ray grid is disposed in or on the rotating frame. Two first flexible hinge elements are connected to the first rotating frame and are aligned along the first axis. The first rotating frame is reversibly rotatable about the first axis. An x-ray arrangement has one or more such suspension devices between an x-ray emitter and an x-ray detector. The articulated flexible elements of the novel device are completely play-free and significantly more cost-effective that separate hinges.

18 Claims, 2 Drawing Sheets

DEVICE FOR SUSPENDING AN X-RAY GRID, ARRANGEMENT WITH AN X-RAY GRID AND METHOD FOR OPERATING AN X-RAY GRID

CROSS-REFERENCE TO RELATED APPLICATION

This application claims the priority, under 35 U.S.C. § 119, of German patent application DE 10 2016 210 529.9, filed Jun. 14, 2016; the prior application is herewith incorporated by reference in its entirety.

BACKGROUND OF THE INVENTION

Field of the Invention

The invention relates to a device for rotatably suspending an x-ray grid, to an arrangement with a rotatably mounted x-ray grid and to a method for operating an x-ray grid. The x-ray grid may also be a scattered radiation grid.

In x-ray imaging, in order to increase the image quality, the scattered radiation is filtered out upstream of the image receiver using a scattered radiation raster (=grid). New production methods permit the construction of scattered radiation rasters with a high aspect ratio (=height of the structure relative to the structure period). They are referred to as "super rasters."

Grids of this type are however not readily usable in conventional x-ray angiography devices, because the focal point of the x-ray emitter moves on account of elastic deformations in the device during movements of the support stands of the angiography device. This results in unwanted shadowing effects and in non-compensatable artifacts in the x-ray imaging.

Interference grids are introduced into the radiation path between the x-ray emitter and the x-ray detector in order to generate a phase contrast image. These grids must be aligned exactly with one another and with the x-ray detector, which involves tilting and canting the grid about a very small angle. The high accuracy requires play-free turning knuckles.

SUMMARY OF THE INVENTION

It is accordingly an object of the invention to provide a device which overcomes the above-mentioned and other disadvantages of the heretofore-known devices and methods of this general type and which provides for a device and an arrangement for rotatably suspending an x-ray grid and a method for operating an x-ray grid, which permit a play-free rotational movement of the suspension with very good accuracy (less than one arc second).

With the foregoing and other objects in view there is provided, in accordance with the invention, a device for suspending an x-ray grid, the device comprising:

a first rotating frame configured to support the x-ray grid therein or thereon; and two first flexible hinge elements connected to said first rotating frame and mounting said first rotating frame for reversible rotation about a first axis.

In other words, in accordance with the invention, the x-ray grid is mounted in one or a number of rotating frames, which can each be rotated about an axis by means of articulated or torsion spring-type flexible elements. The flexible elements are preferably embodied as plastic hinges or spring hinges. The frames together can form a gimbal.

The invention claims a device for suspending an x-ray grid. The device has a first rotating frame which can be rotated about a first axis, in or on which the x-ray grid is arranged, and two articulated first flexible elements which are connected to the first rotating frame and are aligned along the first axis, about which flexible elements the first rotating frame is mounted in a reversibly rotatable manner.

The invention is advantageous in that compared with known solutions the use of articulated flexible elements is completely play-free and significantly more cost-effective.

In accordance with an added feature of the invention, the first flexible elements can be embodied as plastic hinges.

In accordance with an additional feature of the invention, the first rotating frame and the first flexible elements can be formed in one piece and from sheet metal. By using a piece of bent sheet metal, two adjustment directions (tilting and canting) can be realized in one single component.

In accordance with a further feature of the invention, the first flexible elements can be embodied as spring hinges.

In a further embodiment, the first rotating frame and the first flexible elements can be formed from plastic.

In accordance with a further embodiment of the invention, the device has a second rotating frame which can be rotated about a second axis, in which the first rotating frame is rotatably arranged, and two articulated second flexible elements which are connected to the second rotating frame and are aligned along the second axis, about which the second rotating frame is mounted in a reversibly rotatable manner.

Furthermore the device can comprise a retaining frame, in which the second rotating frame is rotatably arranged.

In one further embodiment, the first and the second axis can lie in one common plane and be aligned at right angles to one another. The alignment results in a gimbal.

In accordance with again an added feature of the invention, the second flexible elements can be embodied as plastic hinges.

In accordance with again an additional feature of the invention, the second rotating frame and the second flexible elements can be formed in one piece and from sheet metal.

In a further embodiment, the second flexible elements can be embodied as spring hinges.

In one development, the second rotating frame and the second flexible elements can be formed from plastic.

In accordance with again a further feature of the invention, the device has a motor-driven first linear drive, which exerts a force on the first rotating frame, wherein the first rotating frame is deflected about the first axis.

In accordance with again another feature of the invention, the device has a motor-driven second linear drive, which exerts a force on the second rotating frame, wherein the second rotating frame is deflected about the second axis.

In a further embodiment, the first linear drive and the second linear drive can be embodied as a spindle drive.

With the above and other objects in view there is also provided, in accordance with the invention, an arrangement with an x-ray emitter and an x-ray detector, wherein one or more of the novel devices, as outline above, are arranged between the x-ray emitter and the x-ray detector.

In accordance with a concomitant feature of the invention, there is provided a method for operating an x-ray grid with an inventive arrangement, wherein the x-ray grid is tilted and canted about predetermined angles.

Other features which are considered as characteristic for the invention are set forth in the appended claims.

Although the invention is illustrated and described herein as embodied in a device for suspending an x-ray grid, arrangement with an x-ray grid and method for operating an x-ray grid, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
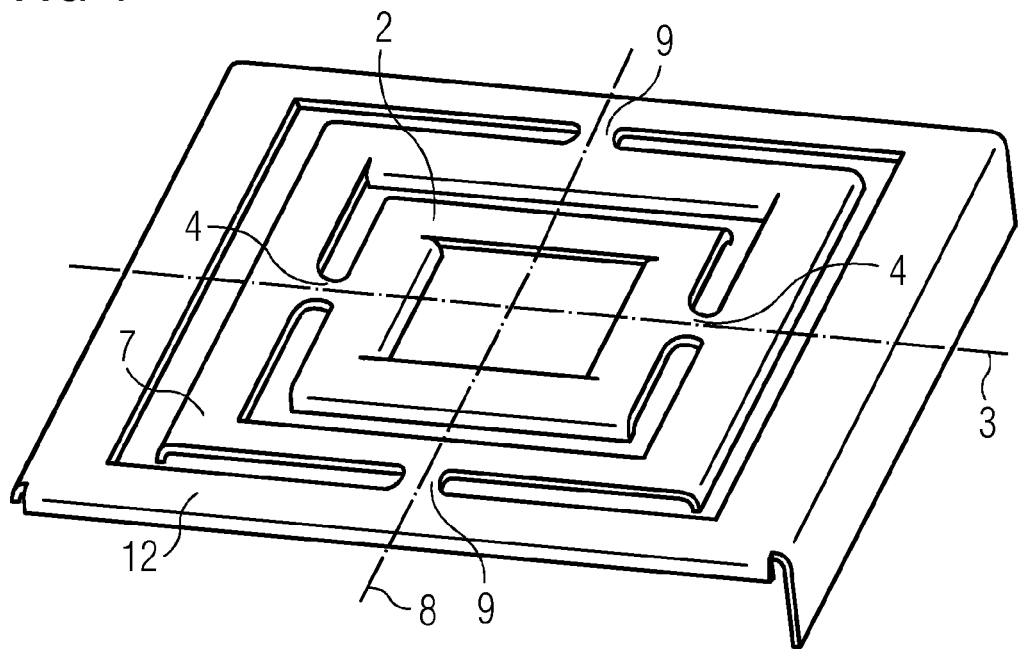
FIG. 1 is a perspective view of a device for rotatably suspending an x-ray grid.

Referring now to the figures of the drawing in detail and first, particularly, to FIG. 1 thereof, there is shown a device for suspending an x-ray grid. The device is manufactured in one piece from sheet metal. The device consists substantially of three parts. A retaining frame 12 forms an outer part. A second, rotating frame 7 is rotatably mounted inside the retaining frame 12 about the second axis 8 by way of two second flexible elements 9. The second flexible elements 9 are embodied as plastic hinges.

In plastic theory a plastic hinge refers to a hinge which is embodied by the bearing structure if the yield strength is exceeded. It is therefore not a real hinge as an independent component, but instead a point on a construction or a bearing structure placed under stress as a hinge, which as far as possible is characterized by a large mechanical deformability. The prerequisite for this is generally the use of a ductile material which permits significant plastic deformations without completely collapsing.

A first rotating frame 2 is rotatably mounted in the second rotating frame 7 about a first axis 3 by way of two first flexible elements 4. The flexible elements are also plastic hinges. An x-ray grid 1 (see, FIG. 2) can be arranged on or in the first rotating frame 2.

The first and second flexible elements 4, 9 are play-free and allow for very accurate rotational movements. The device is gimbaled, since the first and the second axes 3, 8 lie in a common plane and they are aligned orthogonally, at right angles, to one another.

In a further embodiment, the device can also be manufactured from plastic material, as opposed to a metal sheet. The first and second flexible elements 4, 9 are then embodied as spring hinges.

Figure 2:
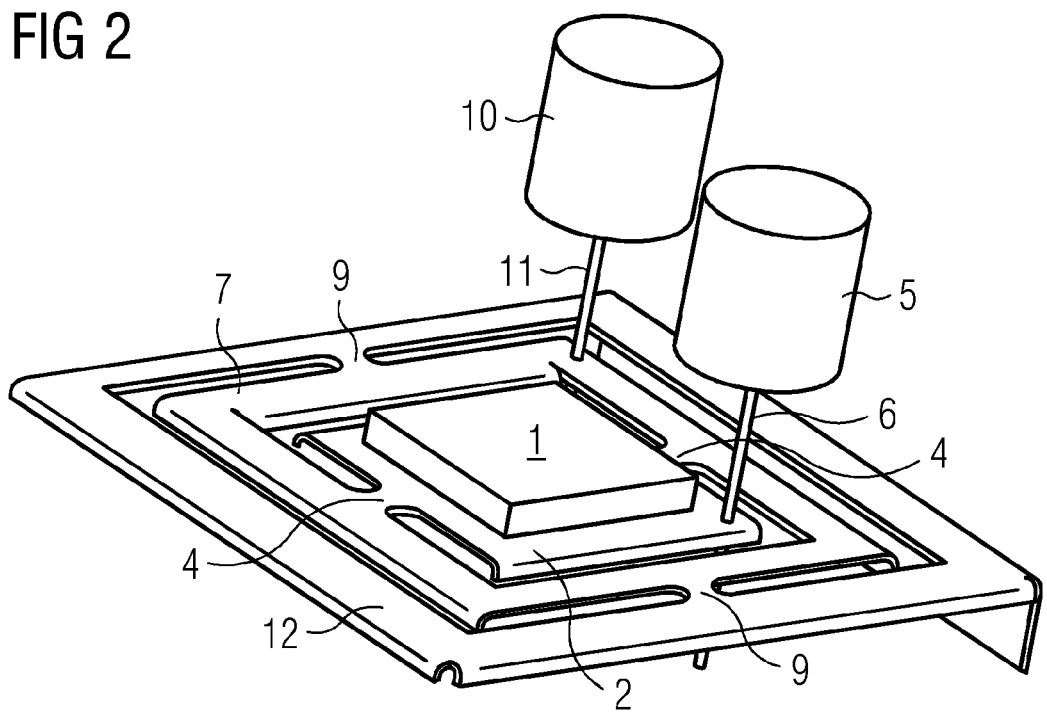
FIG. 2 is a similar view of a device for rotatably suspending an x-ray grid with linear drives.

FIG. 2 shows the device according to FIG. 1. An x-ray grid 1, for instance a scattered radiation grid or an interference grid, is mounted on the first rotating frame 2. By means of the first spindle 6 the first rotating frame 2 is rotated about the first flexible elements 4 with the motor-driven first linear drive 5.

A rotational movement about the second flexible elements 9 is carried out by means of the second rotating frame 7 at right angles to this rotational direction. For this purpose the second spindle 11 of the motor-driven second linear drive 10 grips the second rotating frame 7.

During operation the x-ray grid 1 can be inclined and tilted about predeterminable angles with the aid of the first and second linear drives 5 and 10.

Figure 3:
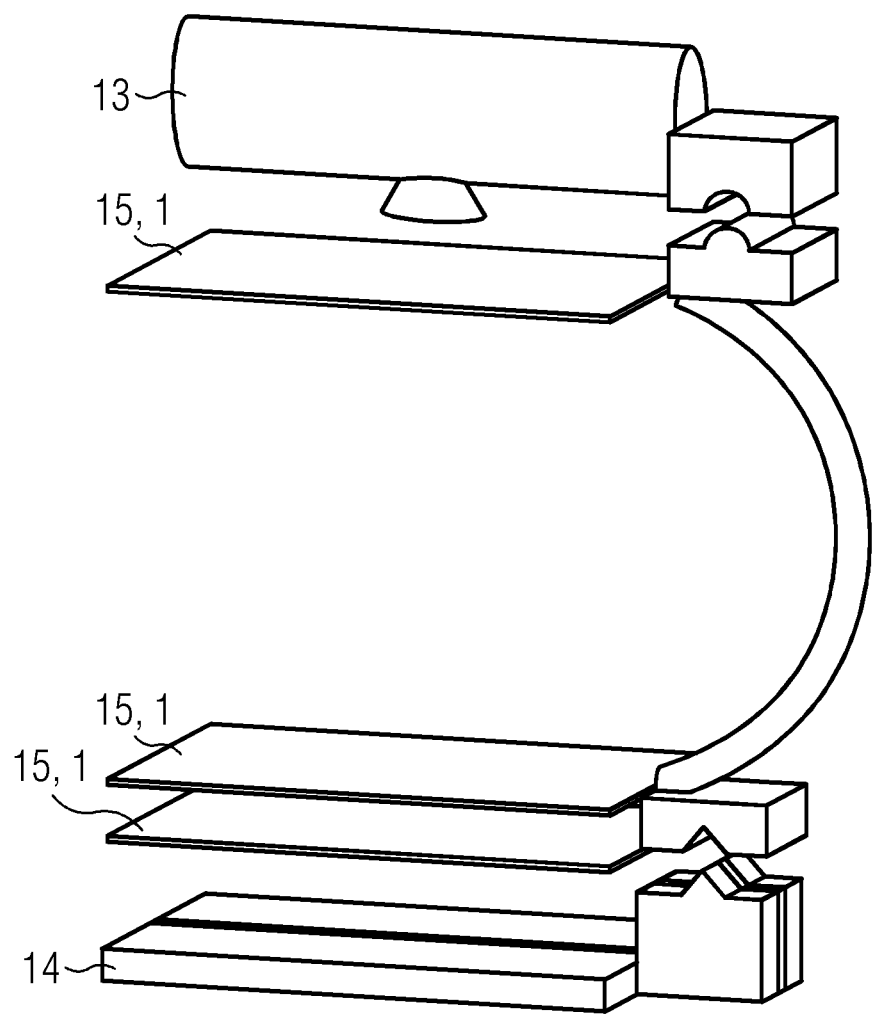
FIG. 3 is a perspective view showing an arrangement with a rotatable x-ray grid.

FIG. 3 shows an interferometric arrangement for phase contrast imaging with three phase grids 1 in a grid suspension 15 in each case, which can be embodied in accordance with the device from FIG. 1 and FIG. 2. The grid suspensions 15 are arranged between an x-ray emitter 13 and an x-ray detector 14.

Although the invention was illustrated and described in more detail by the exemplary embodiments, the invention is not restricted by the disclosed examples and other variations can be derived therefrom by the person skilled in the art without departing from the protective scope of the invention.

The following is a summary list of reference numerals and the corresponding structure used in the above description of the invention:

1 x-ray grid
2 first rotating frame
3 first axis
4 first flexible element
5 first linear drive
6 first spindle
7 second rotating frame
8 second axis
9 second flexible element
10 second linear drive
11 second spindle
12 retaining frame
13 x-ray emitter
14 x-ray detector
15 grid suspension

The invention claimed is:

1. A device for suspending an x-ray grid, the device comprising:
    a first rotating frame configured to support the x-ray grid therein or thereon; and
    two first flexible hinge elements connected to said first rotating frame and mounting said first rotating frame for reversible rotation about a first axis.

2. The device according to claim 1, wherein said first flexible hinge elements are plastic hinges.

3. The device according to claim 1, wherein said first rotating frame and said first flexible hinge elements are formed in one piece from sheet metal.

4. The device according to claim 1, wherein said first flexible hinge elements are spring hinges.

5. The device according to claim 1, wherein said first rotating frame and said first flexible elements are formed from plastic material.

6. The device according to claim 1, which further comprises:
    a second rotating frame rotatably mounted about a second axis, wherein said first rotating frame is rotatably mounted in said second rotating frame; and
    two second flexible hinge elements connected to said second rotating frame and aligned along the second axis, about which said second rotating frame is reversibly rotatably mounted.

7. The device according to claim 6, which further comprises a retaining frame, in which said second rotating frame is rotatably arranged.

8. The device according to claim 6, wherein the first axis and the second axis lie in a common plane and extend perpendicularly to one another, wherein a gimbal is formed.

9. The device according to claim 6, wherein said second flexible hinge elements are plastic hinges.

10. The device according to claim 6, wherein said second rotating frame and said second flexible hinge elements are formed in one piece and from sheet metal.

11. The device according to claim 6, wherein said second flexible hinge elements are spring hinges.

12. The device according to claim 6, wherein said second rotating frame and said second flexible hinge elements are formed from plastic material.

13. The device according to claim 6, which further comprises:
- a motor-driven first linear drive configured to exert a force on said first rotating frame so as to deflect said first rotating frame about the first axis; and
- a motor-driven second linear drive configured to exert a force on said second rotating frame so as to deflect said second rotating frame about the second axis.

14. The device according to claim 13, wherein each of said first linear drive and said second linear drive is a spindle drive.

15. The device according to claim 1, which further comprises a motor-driven first linear drive disposed to exert a force on said first rotating frame so as to deflect said first rotating frame about the first axis.

16. The device according to claim 15, wherein said first linear drive is a spindle drive.

17. An x-ray arrangement, comprising:
- an x-ray emitter and an x-ray detector; and
- at least one device according to claim 1 disposed between said x-ray emitter and said x-ray detector.

18. A method for operating an x-ray arrangement, the method comprising:
- providing an x-ray arrangement according to claim 17; and
- selectively tilting and canting the x-ray grid about predeterminable angles.

* * * * *